United States Patent [19]

Jenuwine et al.

[11] Patent Number: 5,121,339
[45] Date of Patent: Jun. 9, 1992

[54] LASER WELD FAULT DETECTION SYSTEM

[75] Inventors: David J. Jenuwine, Utica; Jacob N. George, Sterling Heights, both of Mich.

[73] Assignee: General Motors Corporation, Detroit, Mich.

[21] Appl. No.: 568,499

[22] Filed: Aug. 16, 1990

[51] Int. Cl.⁵ .................. G01N 29/14; B23K 26/00
[52] U.S. Cl. .................. 364/507; 364/552; 219/130.01
[58] Field of Search ........... 364/505, 506, 507, 551.01, 364/551.02, 550, 552, 575, 576, 726, 574, 474.08, 477; 73/587, 588, 603, 632; 219/130.01

[56] References Cited

U.S. PATENT DOCUMENTS

| 3,679,865 | 7/1972 | Jesnitzer | 219/130.01 |
|---|---|---|---|
| 3,965,726 | 6/1976 | Vahaviolos | 73/587 |
| 4,007,631 | 2/1977 | Saifi et al. | 73/587 |
| 4,144,766 | 3/1979 | Wehrmeister | 73/587 |
| 4,419,562 | 12/1983 | Jon et al. | 219/130.01 |
| 4,501,149 | 2/1985 | Konno et al. | 73/587 |
| 4,615,027 | 9/1986 | Rajkai et al. | 364/726 |
| 4,633,057 | 12/1986 | Wilson et al. | 219/121.63 |

FOREIGN PATENT DOCUMENTS 0014083  1/1986  Japan ............... 219/124.34

Primary Examiner—Parshotam S. Lall
Assistant Examiner—M. J. Zanelli
Attorney, Agent, or Firm—Howard N. Conkey

[57] ABSTRACT

An on-line, non-destructive method and apparatus monitors a welding process and detects faulty welds by analyzing the average frequency of the airborne radiation emitted from a weld during the welding process. A sequence of measured average frequency values corresponding to sequential blocks of time during the weld are individually compared to a predetermined frequency threshold value. Overall weld integrity is discerned by comparing the number of average frequency values exceeding the threshold value to the number of average frequency values not exceeding the threshold value.

7 Claims, 2 Drawing Sheets

LASER WELD FAULT DETECTION SYSTEM

FIELD OF THE INVENTION

This invention relates to a real-time, non-destructive method and apparatus for detecting improperly welded parts.

BACKGROUND OF THE INVENTION

Automatic welding is commonplace in industry today where autonomous welding machines are preprogrammed to accomplish repetitive tasks. Dimensional variations in welded parts, misalignment of welded parts, impurities in weld materials and perturbations that arise during the weld process can result in improper welds. Any defect in the weld can substantially reduce weld life, degrading product quality and durability. Additionally, the costs of repetitive weld defects that go unnoticed can multiply rapidly.

Weld integrity is not easily discerned, as defects are often hidden in the form of porosity, embrittlement, lack of fusion and lack of penetration. Additionally, the hostile weld environment and the speed of many weld processes make it difficult for an operator to thoroughly inspect a weld without reducing process throughput considerably.

Consequently, industry recognizes the importance of automated fault detection systems in weld processes that can thoroughly scrutinize the weld for hidden defects, and can keep up with the assembly process. Defects should be detected quickly such that the faulty parts can be discarded or repaired, and repeated faults should be diagnosed in their infancy and treated as welding process failures.

Several techniques for detecting improper welds are in the prior art. Conventional off-line techniques periodically take sample parts from the assembly process and analyze them, for example by attempting to break the weld itself. If the weld breaks before the material around the weld breaks, then the weld is assumed to be faulty. These off-line techniques have the disadvantage of slowing the entire 10 weld process and of only analyzing the sample—allowing many untested welds to pass through the system. By increasing the sampling rate, fewer welds can pass through without being tested, but more potentially useful parts are destroyed.

On-line techniques exist in the prior art. Some of these techniques use ultrasonic sensors to sample high frequency weld emissions. The high frequency signals are analyzed to discern weld integrity. The sensors used in these methods are expensive, prone to failure, require accurate positioning with respect to the weld site, and require precise calibration.

Many on-line methods sense and analyze the amplitude of airborne emissions from the weld during the weld process. Such amplitude methods are highly sensitive to the noise in the weld environment, which distorts the sensed signal amplitude and thereby undermines the integrity of the amplitude analysis. Additionally, these methods require precise calibration of the sensors, and can produce erroneous results if the weld conditions are not identical from part to part.

SUMMARY OF THE INVENTION

The subject invention overcomes the limitations of the prior methods as it is an on-line, non-destructive method and apparatus that detects improper welds by analyzing the average frequency of emissions radiated from the weld site during the weld process.

Specifically, sensors are placed at the weld site which transduce radiation from the weld process into an electrical signal. This signal is amplified by a common analog amplifier and then is transmitted to an analog to digital converter. The digital output of the converter is transmitted to a signal processing and storage system. When the weld process is started, this system begins sampling the digital data at a predetermined sampling rate and storing the data in data blocks of predetermined size.

When a data block is full, the data in that block is transformed to the frequency domain and stored as a block of frequency values. The values in this block are then averaged, yielding one scalar value representing the average frequency content of the airborne emissions for that block. The system continues to fill, transform and average these data blocks for the duration of the welding process. At the end of the weld process, the set of scalar values, one from each block, are individually compared to a predetermined threshold value. Scalar values which exceed the threshold value indicate that the corresponding section of that weld is faulty. Furthermore, if the ratio of faulty weld sections to "fault-free" weld sections exceeds a predetermined ratio, the entire weld is diagnosed as defective.

The invention may be used to sense airborne emissions in the audible frequency band. The emission sensors may then be durable, inexpensive audio microphones, and can be placed anywhere within three to six feet from the weld site. Minimal signal filtering and virtually no calibration is required in such a system.

Unlike the discussed prior art, the present invention is non-destructive, operates in real-time, requires minimal calibration, and requires minimal signal filtration. The data collection and analysis process is performed rapidly such that all welds may be analyzed without introducing any delay in the welding process. By analyzing the average frequency content of the emissions, this system is much less sensitive than prior systems to background noise, sensor placement, part to part variations, and different weld applications.

DESCRIPTION OF THE PREFERRED EMBODIMENT

Figure 1:
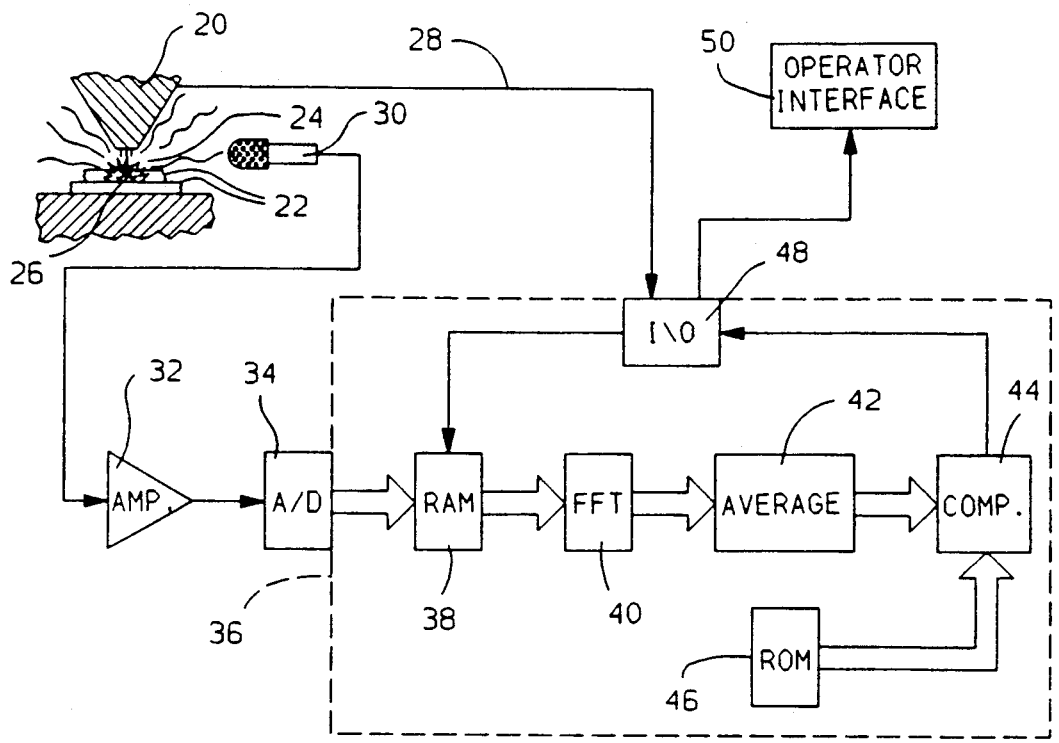
FIG. 1 is a general diagram of the fault detection system for detecting improper welds in accord with this invention.

Referring to FIG. 1, an airborne emission sensing device 30 is placed in proximity to the weld site of a welding tool 20. In this embodiment, the sensing device is placed between three and six feet from the weld site 20. The tool in this embodiment is a conventional laser welding tool, used to attach two metal plates 22 by means of a high energy, visible light beam 24. However, the application of this invention to other welding tools is contemplated by the inventors. The beam 24, when energized, is a continuous, multi-mode beam, directed at multiple points around the desired weld location. The plates 22 are clamped together and are placed in a perpendicular arrangement with respect to the beam 24. Each individual beam is tuned so that its visible light comes to focus at the point where the two plates make contact with each other 26.

When the plates 22 are in place, the tool 20 is energized and an enable signal is immediately transmitted along a conductor 28 attached between the welding tool 20 and an input port 48 of a signal processing and storage system 36. This signal is set to logic '1' when the welding tool 20 is welding the plates and is otherwise reset to logic '0'. The subsequent heating and bonding of the metal plates creates airborne emissions which have been found to characterize the integrity of the bonding process. In this embodiment, a simple audio microphone 30 is used to measure emissions in the 0-20 kHz range. In other embodiments, the sensor can be any device capable of sensing emissions in an applicable frequency band of interest.

The microphone 30 has a continuous analog output which is connected to an amplifier 32, the output of which is connected to an analog to digital converter 34. The digital output of the converter 34 is connected to the signal processing and storage system 36 which samples the digital data at a predetermined sampling rate, and stores the resultant discrete digital data in random access memory 38. At predetermined time intervals, the stored data is transformed to the frequency domain using standard Fast Fourier Transform techniques. In this embodiment, a dedicated Burr Brown ZPB-3211 single chip digital signal processor 40 is used solely to make this transformation, with which a 512 entry data block may be transformed in less than 20 milliseconds.

Next, the frequency data is communicated to an averaging block 42 which averages the frequency data, to provide an average frequency value for the process. That value is transmitted to a comparator 44, where it is compared to a predetermined threshold value which has been stored in the read only memory 46 of the signal processing and storage system 36. The weld is diagnosed as faulty if the average frequency value exceeds the predetermined value. Upon diagnosing a weld as bad, a message is sent through an output port 48 to an operator interface 50, advising the operator of the fault. The system operator may then attempt to cure the fault by repositioning the parts with respect to the weld beam, reclamping the parts, or adjusting the focal point of the beam. The weld process, or a part thereof, is then repeated with the fault detection invention again checking the integrity of the weld. If the fault is determined to be incurable, the operator may remove the parts from the weld zone and discard them or attempt an off-line manual repair.

The central processor in the processing system takes the form of a standard digital computer, such as a Motorola 68030 32-bit, single-chip microcomputer. The computations used to carry out the principles of this invention are performed by this processor, with the exception of the transformation of the data to the frequency domain, which is carried out by the Burr Brown digital signal processor 40, as discussed. The principles of this invention are implemented in the form of an operating program stored in the read only memory 46 of the central processor.

Figure 2:
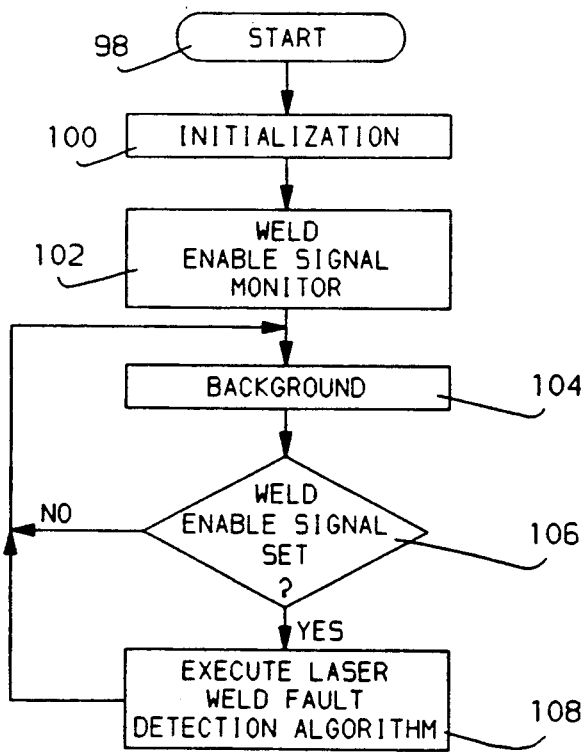
FIGS. 2 and 3 are computer flow diagrams showing the operation of the controller in which the principles of this invention take place.

Referring to FIG. 2, when power is first applied to the system, the control program is entered at step 98, and proceeds to step 100 where the controller provides for system initialization. For example, at this step data constants are transferred from ROM locations to RAM locations and counters, pointers and flags are initialized.

After the initialization step the controller proceeds to step 102, where the system starts a routine to periodically monitor the weld enable signal, which is set to logic '1' when a weld is in progress and is otherwise reset to logic '0'. The controller then proceeds to a background loop at step 104 which is continuously repeated. This loop may include system diagnostic and maintenance routines. The loop also includes a routine to monitor the weld enable signal shown at step 106, such that the fault detection algorithm incorporating the principles of this invention will be executed at step 108 whenever this routine senses that a new weld has begun.

Figure 3:
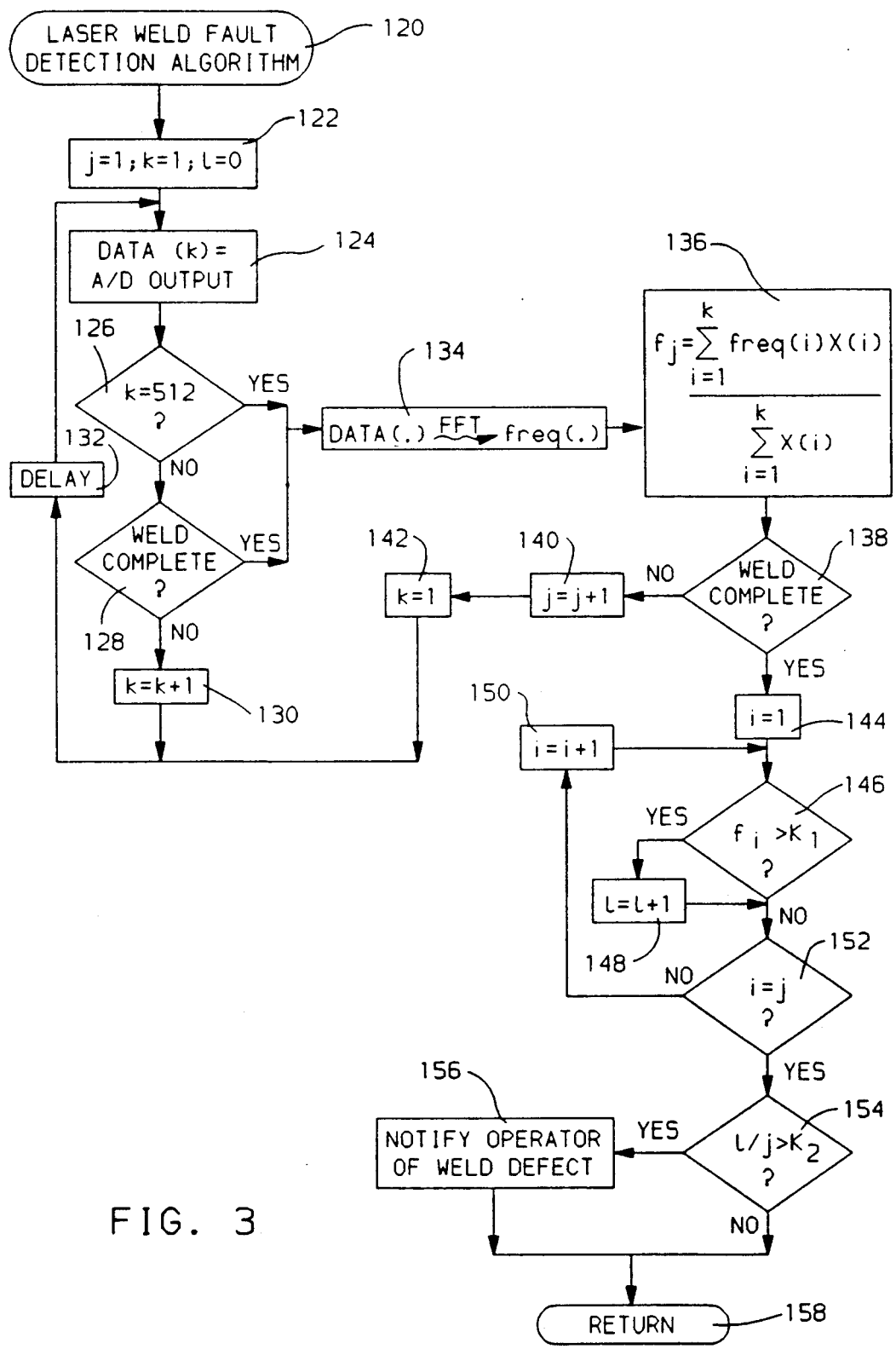

This fault detection algorithm is illustrated in FIG. 3, and is entered at step 120. Generally, the algorithm senses and stores radiation from a weld during the weld process into data blocks of predetermined size. In this embodiment, the blocks contain 512 data points. When a block is full, the data contained therein is transformed to the frequency domain and is then averaged yielding one scalar average frequency value for that block. This is continued for the duration of the welding process. When the weld is complete, each scalar value is compared to a predetermined value to determine the integrity of the weld.

Specifically, at the start of the weld, the algorithm proceeds to step 122, where temporary variables used in the present execution of the algorithm are initialized. Next, at step 124, the controller reads the output of the analog to digital (A/D) converter and stores the digital value as the kth entry in the 512 entry data block. The controller then, at step 126, checks to see if the block is full. If the block is not full, the controller reads the weld enable line at step 128. If this line is at digital '1' such that the welding process is still in progress, the controller increments the storage pointer k at step 130 for storage of the next entry in the block. The controller then delays for a predetermined amount of time at step 132 before repeating the process starting at step 124. In the preferred embodiment, the delay is set up so that new data is read from the A/D converter every fifty microseconds.

If either the 512 entry data block is full at step 126 or the weld enable line is at digital '0' at signifying the completion of the present weld, he controller executes steps 134 through 158 to analyze the emissions from the weld. Specifically, at step 134, the data in the block, whether the block is full or not, is transformed to the frequency domain using standard Fast Fourier Transform techniques.

The frequency data is then averaged at step 136 to arrive at one scalar value $f_j$ which is the average frequency for the jth block of data, according to the following equation $$f_j = \left( \sum_{i=1}^{k} \text{freq}(i) X(i) \right) / \left( \sum_{i=1}^{k} X(i) \right)$$

where freq(i) is the frequency of the ith entry in memory, and X(i) is the magnitude of the ith frequency component.

Next, the weld enable line is read at step 138. If it is set to a logic '1', signifying that the weld is still in progress, the pointer for storing the average frequency data j is incremented at step 140, the pointer for storing data in the data block k is reset for the next block at step 142, and the controller returns to the delay block 132 to delay before starting to fill the next 512 entry block.

Alternatively, if the weld enable line is reset to logic '0' at step 138, signifying completion of the weld, the controller executes steps 144 through 158 to analyze the stored series of average frequency points. Starting with step 144, the controller resets the index i to point at the start of the sequence of average frequency data values. Next, at step 146, the controller compares the ith average frequency point to a predetermined threshold value $K_1$.

Experimentation has shown that the creation of a faulty weld produces emissions with substantially higher average frequency than the creation of a "fault-free" weld. $K_1$ is determined through experimentation where, for given materials and a given welding system, the average frequency is measured from known faulty and known fault-free welds. A region exists between the measured average frequency values of these two types of welds, and $K_1$ is determined as the midpoint of that region.

Returning to step 146, if the average frequency value $f_i$ exceeds the threshold value $K_1$, an excursion counter is incremented at step 148. Otherwise, the controller goes back and examines the next average frequency point via steps 150 and 152. This process continues until the controller determines at step 152 that it has compared all of the frequency points to $K_1$.

The fraction of faulty frequency points to overall frequency points is then compared at step 154 to a cutoff fraction, $K_2$. $K_2$ is derived as a function of the desired quality of the weld and of the predicted error in the frequency measurements. Imperfections may exist in any weld but may not significantly impact the integrity of the bond between the welded parts. Additionally, substantial inaccuracies often exist in the data acquisition and analysis steps of this algorithm. $K_2$ is the tolerance means by which a certain degree of weld imperfection and data gathering error is tolerated without diagnosing a weld as faulty.

Returning to FIG. 3, if, at step 154, the fraction of frequency excursions exceeds $K_2$, a signal is sent to the system operator at step 156 to identify the weld as defective. The operator may then, at his discretion, attempt any conventional cure, or may discard the parts, depending in the severity and curability of the defect. The controller then, at step 158, returns to the background routine which will continuously repeat until the weld enable line is again set to a logic '1', indicating the start of the next weld. If the fraction of frequency excursions does not exceed the cutoff value, the controller directly returns to the background routine at step 158.

This algorithm, starting again at step 120, will continue to repeat while the fault detection controller is operating. The entire algorithm is executed for a given weld in less than one second, such that no interruption or delay is introduced into the automatic weld process.

The foregoing description of a preferred embodiment for the purpose of explaining the principles of this invention is not to be considered as limiting or restricting the invention since many modifications may be made by the exercise of skill in the art without departing from the scope if the invention.

The embodiments of the invention in which an exclusive property or privilege is claimed are defined as follows:

1. A method for real-time, non-destructive detection of improperly welded parts comprising the steps of:
   transducing airborne radiation emitted by said welded parts during a welding process into an analog signal;
   transforming said analog signal over a predetermined period of time into its equivalent frequency signal in the frequency domain;
   determining an average frequency of said frequency signal;
   comparing said average frequency to a predetermined frequency threshold value;
   signaling the presence of an improper weld when said average frequency exceeds said predetermined frequency threshold value.

2. The method of claim 1, wherein said airborne radiation comprises airborne radiation in the 0–20 kHz frequency range.

3. The method of claim 1, wherein said welding process comprises a laser welding process, wherein a laser is the energy source by which said parts are welded together.

4. The method of claim 1, wherein said transforming step comprises the step of processing said analog signal through a Fast Fourier Transform procedure, by which said analog signal is transformed into its frequency equivalent in the frequency domain.

5. An apparatus for real-time, non-destructive detection of improperly welded parts comprising:
   signal transducing means by which airborne radiation emitted from a weld site during a welding process is transduced into an analog signal;
   transforming means for transforming said analog signal over a predetermined time period into its equivalent frequency signal in the frequency domain;
   average frequency determining means for determining an average frequency of said frequency signal;
   frequency comparing means for comparing said average frequency to a predetermined threshold frequency;
   fault signaling means for signaling the presence of an improper weld when said average frequency exceeds said predetermined threshold frequency.

6. The apparatus of claim 5, wherein said airborne radiation comprises radiation in the 0–20 kHz frequency range.

7. The apparatus of claim 5, wherein said transforming means comprises means for processing said analog signal through a standard Fast Fourier Transform procedure by which said analog signal is transformed into its frequency equivalent in the frequency domain.

* * * * *